United States Patent [19]

Richter et al.

[11] Patent Number: 4,560,738

[45] Date of Patent: Dec. 24, 1985

[54] PEST-COMBATING AGENT HAVING INCREASED DURATION OF ACTION

[75] Inventors: Roland Richter, Cologne; Paul Reinecke, Leverkusen; Hanns P. Müller, Odenthal; Gerhard Bonse, Cologne; Wilhelm Brandes, Leichlingen, all of Fed. Rep. of Germany

[73] Assignee: Bayer Aktiengesellschaft, Leverkusen, Fed. Rep. of Germany

[21] Appl. No.: 524,955

[22] Filed: Aug. 19, 1983

[30] Foreign Application Priority Data

Sep. 4, 1982 [DE] Fed. Rep. of Germany ....... 3232917
Oct. 15, 1982 [DE] Fed. Rep. of Germany ....... 3238358

[51] Int. Cl.⁴ .......................................... C07C 125/06
[52] U.S. Cl. ..................................... 528/62; 528/73; 544/182; 548/163; 548/262; 548/306; 564/38; 514/395; 514/383; 514/367; 514/242
[58] Field of Search .................. 528/73, 62; 424/249, 424/269, 270, 273 R, 322; 544/182; 548/163, 262, 306; 564/38

[56] References Cited

FOREIGN PATENT DOCUMENTS 2901060 7/1980 Fed. Rep. of Germany .
2910356 9/1980 Fed. Rep. of Germany .
2912289 10/1980 Fed. Rep. of Germany .

OTHER PUBLICATIONS

Beyer Lehrbuch der Organischen Chemie (1968), p. 147.

*Primary Examiner*—Maurice J. Welsh
*Attorney, Agent, or Firm*—Sprung Horn Kramer & Woods

[57] ABSTRACT

A novel pest-combating agent of increased duration of action is produced by reacting a pest-combating agent having at least one hydrogen atom active in a Zerewitinoff reaction other than a hydrogen atom which is part of a carbamic acid ester group

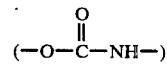

with a polyether isocyanate, the reaction with the polyether isocyanate taking place on said other hydrogen atom.

14 Claims, No Drawings

PEST-COMBATING AGENT HAVING INCREASED DURATION OF ACTION

The present invention relates to new compounds, a process for their preparation and their use as pest-combating agents having an increased duration of action.

Agents having an increased duration of action, that is to say with delayed release of the active compound (slow release properties), are compounds in which a molecule of active compound is chemically bonded to a polymeric carrier and which release the active compound component from the polymeric carrier by hydrolysis or depolymerization under use conditions.

Examples of known processes for the preparation of such a combination are the linking of an active compound containing a reactive group (for example an isocyanate group) with a suitable polymeric carrier, such as polyvinyl alcohol (specification U.S. Pat. No. 4,267,281) or with a polymerizable monomer, such as acrylic acid (specification U.S. Pat. No. 4,225,693) or with a copolymer containing glycidyl groups (DE-OS (German Published Specification) No. 2,819,340). The disadvantage of this process is that either the active compound must be chemically modified to produce the functional group, for example by conversion of an amine group into an isocyanate group, which is associated with loss of expensive active substance, or derivatives can be formed exclusively from only those active compounds which contain a hydroxyl group, or, on subsequent polymerization additional factors besides hydrolysis, such as the rate of depolymerization and the diffusion from the polymeric structure, influence the release of the active molecule embedded in the polymer, which considerably restricts use because of the poor reproducibility.

It is known to link active compounds containing a hydrogen atom active in Zerewitinoff reactions to a polyether containing one OH or NH monofunctional group via a coupling member possessing two groups which are reactive towards hydrogen atoms active in Zerewitinoff reactions; compare DE-OS (German Published Specification) No. 2,901,060, DE-OS (German Published Specification) No. 2,910,356 and DE-OS (German Published Specification) No. 2,912,289. This process is intended to improve the solubility of biologically active compounds in water and lower aliphatic alcohols. In spite of a modification which changed their molecular weight, the active compounds retain their full action, and even acquire an additional systemic action.

Nothing is known of increasing the duration of action of plant protection agents by forming these derivatives.

The present invention relates to new compounds, characterized in that they can be prepared by reacting a pest-combating agent having at least one hydrogen atom active in a Zerewitinoff reaction with polyether isocyanates with the prerequisite that the reaction with the polyether isocyanate does not take place on a hydrogen atom which is part of a carbamic acid ester group

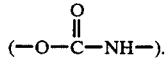

The present invention also relates to the process for the preparation of the new compounds, which is characterized in that pest-combating agents having at least one hydrogen atom active in Zerewitinoff reactions are reacted with polyether isocyanates, with the prerequisite that the reaction with the polyether isocyanate does not take place on a hydrogen atom which is part of a carbamic acid ester group

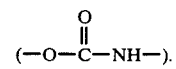

The term hydrogen active in Zerewitinoff reactions is understood as meaning a hydrogen atom which is bonded, in an organic compound, to a center which exerts a highly electron-withdrawing action, in comparison with a C atom of a hydrocarbon. In the narrower sense, active in Zerewitinoff reactions means an H atom which is active in the sense of the reaction: $CH_3MgI + H-X \rightarrow CH_4 + IMgx$ (see also Beyer "Lehrbuch der organischen Chemie" ("Textbook of organic chemistry") (1968) page 147).

The term pest-combating agents is understood as meaning insecticides, acaricides, nematicides, fungicides, bactericides, microbicides, virucides, algicides, herbicides, plant growth regulators and compounds which influence the growth of individual or all stages in the development of insects or acarids. These agents are used in the areas of agriculture and forestry and in the domestic, hygiene and animal breeding sectors.

The compounds according to the invention have an increased duration of action in comparison with the starting active compounds. When the new active compounds are used, it is therefore in many cases unnecessary to apply one and the same active compound several times. The use of the new compounds depends on the use of the pest-combating agents used as the starting substance for their preparation.

The following pest-combating agents which can be used as starting substances may be mentioned as being preferred:

(a) active compounds which contain one or more aminic groups having at least one free NH radical, it being possible for the NH radical to be part of a heterocyclic radical, (b) active compounds containing one or more hydrazine groups having at least one free NH radical, it being possible for the hydrazine group to be part of a heterocyclic radical, (c) active compounds containing one or more quanidine groups having at least one free NH radical, it being possible for the guanidine group to be part of a heterocyclic radical, (d) active compounds containing one or more alcoholic hydroxyl or mercapto groups, (e) active compounds containing one or more phenolic hydroxyl or mercapto groups, (f) active compounds containing one or more carboxylic acid amide groups having at least one free NH radical, it being possible for the carboxylic acid amide group to be part of a heterocyclic radical, and (g) active compounds containing one or more urea groups having at least one free NH radical, it being possible for the urea group to be part of a heterocyclic radical.

Specific compounds which may be mentioned are:

From group (a) active compounds containing a free primary or secondary amino group, such as, for example, methyl N-(N'-6-aminophenyl-thiocarbamoyl)-carbamate and heterocyclic compounds having free amino groups, such as 2-amino-1,3,4-thiadiazoles, 5-amino-5-chloro- or bromo-2-phenyl-pyridazin-3-ones or 4-chloro-5-methylamino-2-(4-trifluoromethylphenyl)-pyridazin-3-one.

From group (b): active compounds from the 4-amino-1,2,4-triazine series, such as, for example, 4-amino-6-tert.-butyl-3-(methylthio)-1,2,4-triazin-5(4H)-one and 4-amino-3-methyl-6-phenyl-1,2,4-triazin-5(4H)-one, or maleic acid hydrazide and 3-methyl-4-(2-chlorophenyl-hydrazones)-1,2-oxazol-5-one, O,O-diethyl O-(3-methyl-5-pyrazolyl)thionophosphate.

From group (c): active compounds, such as, for example, 3-amino-1,2,4-triazole, 2-chloro-4-ethylamino-6-isopropylamino-1,3,5-triazine, 2-chloro-4-ethylamino-6-(1-cyano-isopropylamino)-1,3,5-triazine, 6-(2-chloroanilino)-2,4-dichloro-1,3,5-triazine and methyl 2-benzimidazolecarbamate and methyl 4- or 5-methyl-benzimidazolecarbamate.

From group (d): active compounds from the diphenylcarbinol series, such as, for example, 1,1-bis-(4-chlorophenyl)-2,2,2-trichloroethanol and isopropyl 2,2-bis-(4-chlorophenyl)-2-hydroxy-acetate, phosphonic acid esters containing hydroxyl groups, such as, for example, O,O-dimethyl(1-hydroxy-2,2,2-trichloroethyl)-phosphonate, or 3,3-dimethyl-2-hydroxy-1-(4'-phenyl-phenoxy)-1-(1,2,4-triazol-1-yl)-butane or 9-(carbomethoxy)-2-chloro-9-hydroxy-fluorene and 4-hydroxy-3-(1,2,3,4-tetrahydronaphth-1-yl)-2H-chromenone.

From group (e): active compounds, such as, for example, 6-tert.-butyl-2,4-dinitrophenol, or heteroaromatics which carry hydroxyl groups, such as, for example, 3-hydroxy-5-methyl-1,2,-oxazole, 5-butyl-2-(dimethylamino)-4-hydroxy-6-methyl-pyrimidine or 5-butyl-2-(ethylamino)-4-hydroxy-6-methyl-pyrimidine.

From group (f): active compounds from the phosphoric acid ester series, such as, for example, O,O-dimethyl S-(methylaminocarbonyl-methylene)dithiophosphate and O,O-dimethyl S-(methylaminocarbonyl-methylene)thiophosphate or the phosphoric acid amide O,S-dimethylthionophosphoramide, and heterocyclic compounds in which the amide structure is part of the heterocyclic radical, such as 2-thiono-4-oxo-1,3-thiazolidine.

From group (g): active compounds from the 3-aryl-1,1-dimethylurea series, such as, for example, 3-(3,4-dichlorophenyl)-1,1-dimethylurea, or ureas which contain a heterocyclic radical as a substituent, such as, for example, 1-isobutylaminocarbonyl-2-imidazolidinone, 1,3-dimethyl-1-(5-tert.-butyl-1,3,4-thiadiazol-2-yl)-urea, 1,3-dimethyl-1-(5-trifluoromethyl-1,3,4-thiadiazol-2-yl)-urea and 1-(benzo-1,3-thiazol-2-yl)-1,3-dimethylurea; and furthermore active compounds in which the urea structure is completely present as part of the heterocyclic radical, such as, for example, 4-trichloromethyl-mercapto-3,5-dioxo-1,2,4-triazolidine, 3-(2-butyl)-5-bromo-6-methyl-uracil or 3-cyclohexyl-5,6-trimethyleneuracil, and acylureas of the general formula (I),

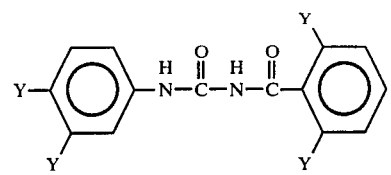

wherein
Y represents hydrogen, halogen and halogenoalkyl or halogenoalkoxy with 1–4 C atoms.

Particular examples which may be mentioned are: herbicides, such as, for example, 4-amino-6-tert.-butyl-3-(methylthio)-1,2,4-triazin-5(4H)-one, 4-amino-3-methyl-6-phenyl-1,2,4-triazin-5(4H)-one, 3-(3,4-dichlorophenyl)-1,1-dimethylurea, 1-(benzo-1,3-thiazol-2-yl)-1,3-dimethylurea and 1,3-dimethyl-1-(5-ethylsulphonyl-1,3,4-thiadiazol-2-yl)-urea; insecticides, such as, for example, O,O-dimethyl(1-hydroxy-2,2,2-tirchloroethyl)-phosphonate and O,S-dimethyl-thionophosphoramide, and fungicides, such as, for example, 2-(2-furyl)-benzimidazole, 6-(2-chloroanilino)-2,4-dichloro-1,3,5-triazine, 3,3-dimethyl-2-hydroxy-1-(4'-phenyl-phenoxy)-1-(1,2,4-triazol-1-yl)-butane and methyl 2-benzimidazolecarbamate.

The fungicidal active compounds from the alkyl 2-benzimidazole-carbamate series of the general formula (II)

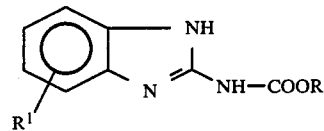

wherein
R represents alkyl with 1–4 C atoms and
$R^1$ represents alkyl with 1–6 C atoms or hydrogen, are to be particularly singled out.

The following polyether isocyanates of the general formula (III) used as starting substances may be mentioned as being preferred

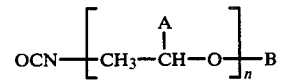

in which
A represents hydrogen or methyl,
n represents an integer between 1 and 101 and
B represents $C_{1-4}$-alkyl or the radical —$C_{1-4}$-alkyl—NCO.

The preparation of the polyether isocyanates is known. They are obtained, for example, by phosgenation of corresponding polyethers with amino end groups such as described in specification U.S. Pat. No. 3,370,077 and in specification U.S. Pat. No. 4,313,764, or by conversion of the amino-polyethers into ureas and urethanes, which are then split under the influence of heat to give the corresponding isocyanates (DE-OS (German Published Specification) Nos. 2,943,481, 2,943,551 and 3,047,898).

Monofunctional polyether isocyanates of the general formula (III) in which n=2—7, A=hydrogen and B=$C_{1-4}$-alkyl are preferably used. These polyether isocyanates are liquid, single compounds which can be distilled at a precisely defined boiling point.

Specific preferred compounds which may be mentioned are: 3,6-dioxaheptyl isocyanate, 3,6-dioxadecyl isocyanate and 3,6,9-trioxadecyl isocyanate.

The compounds according to the invention can advantageously be prepared in the manner described below:

If, for example, 3,6-dioxadecyl isocyanate and methyl 2-benzimidazolecarbamate (MBC), as the active compound, are used, the process according to the invention can be carried out as follows:

The active compound is dissolved or suspended in an inert, anhydrous solvent, for example toluene, in a stirred apparatus, and an equimolar amount of the isocyanate is added. The mixture is then stirred at 25° to 140° C., preferably 60° to 110° C., with exclusion of moisture. The reaction has proceeded to completion when no further isocyanate can be detected in the reaction mixture by IR spectroscopy, or when the starting substance which has previously been suspended has dissolved completely. The mixture is worked up in the customary manner, for example by distilling off the solvent. The new compound has the formula (IV)

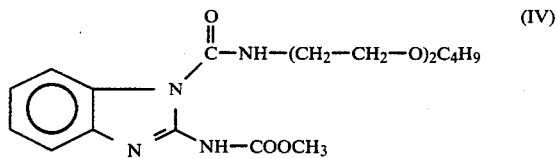

The other compounds according to the invention can be prepared in an analogous manner; in the case of active compounds containing NH of low basicity, such as ureas or amides, which are used as starting substances, it may be appropriate to add 0.1 to 1 mol% of a catalyst which accelerates the reaction, such as those known from polyurethane chemistry, for example dibutyl-tin dilaurate or tin octoate.

Solvents which are used in the preparation of the compounds according to the invention are: hydrocarbons, such as toluene and xylene, chlorinated hydrocarbons, such as $CCl_4$, $CHCl_3$ and $CH_2Cl_2$, esters and ketones, such as ethyl acetate, butyl acetate, acetone and ethyl methyl ketone, ethers, such as dioxane, tetrahydrofuran or di-isopropyl ether, and acetonitrile and DMF.

Suitable catalysts are, in addition to the dibutyl-tin dilaurate and tin dioctoate already mentioned, zinc acetylacetonate and tertiary amines, such as triethylenediamine, 1,8-diazabicyclo[5,4,0]-undec-7-ene or dimethylcyclohexylamine.

The reaction is in general carried out under normal pressure. The starting substances are in general employed in equimolar proportions. An excess of one or the other of the components provides no advantages.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides. Examples of insecticides include phosphoric acid esters, carbamates, carboxylic acid esters, chlorinated hydrocarbons, phenylureas, substances produced by micro-organisms and the like.

The active compounds according to the invention can furthermore be present in their commercially available formulations and in the use forms prepared from these formulations as mixtures with synergistic agents. Synergistic agents are compounds which increase the action of the active compounds, without the synergistic agent added having itself to have an effective action.

The content of active compound in the use forms prepared from the commercially available formulations can vary within wide ranges. The active compound concentration of the use forms can be from 0.0000001 up to 95% by weight active compound, preferably between 0.0001 and 1% by weight.

The active compounds are used in the customary manner suitable for the use forms.

PREPARATION EXAMPLES

In the following text, the process according to the invention is illustrated with the aid of a few examples, but without restricting the subject of the invention to these examples.

EXAMPLE 1

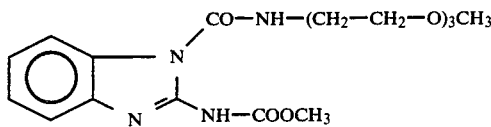

95.6 g (0.5 mol) of methyl 2-benzimidazolecarbamate are suspended in 1,000 ml of anhydrous toluene, 94.5 g (0.5 mol) of 3,6,9-trioxadecyl isocyanate are added and the mixture is stirred at 80° C. for 7 hours under an inert gas and with exclusion of moisture. After this period, the isocyanate band at 2260 cm$^{-1}$ in the IR spectrum has disappeared and the product has dissolved, apart from a minimal residue. The unreacted active compound is then filtered off, and the toluene is subsequently completely distilled off in vacuo. 180.3 g (=95% of theory) of a solid having a melting point of 148°–150° C. are obtained. The adduct shows a stable MH⊕ molecular ion 381 in the mass spectrum; content of active compound: 50%.

The substances listed in the examples which follow are also prepared by the methods described in Example 1.

EXAMPLE 2

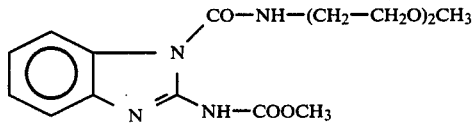

157 g (=95% of theory) of methyl 1-(3,6-dioxaheptylcarbamoyl)-2-benzimidazolecarbamate of molecular mass 336 (MH⊕ in the mass spectrum) are obtained from 95.6 g (0.5 mol) of methyl 2-benzimidazolecarbamate and 72.5 g (0.5 mol) of 3,6-dioxaheptyl isocyanate.

EXAMPLE 3

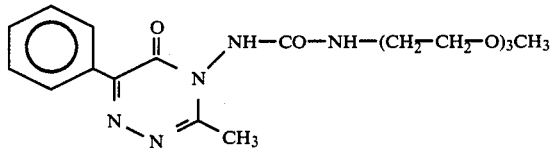

189 g (=97% of theory) of a viscous product of molecular mass 391 (MH⊕ in the mass spectrum) are obtained from 101 g (0.5 mol) of 4-amino-3-methyl-6-phenyl-1,2,4-triazin-5(4H)-one and 94.5 g (0.5 mol) of 3,6,9-trioxadecyl isocyanate.

EXAMPLE 4

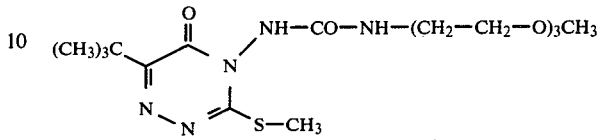

197 g (=98% of theory) of a viscous product of molecular mass 403 (MH⊕ in the mass spectrum) are obtained from 107 g (0.5 mol) of 4-amino-6-tert.-butyl-3-(methylthio)-1,2,4-triazin-5(4H)-one and 94.5 g (0.5 mol) of 3,6,9-trioxadecyl isocyanate.

EXAMPLE 5

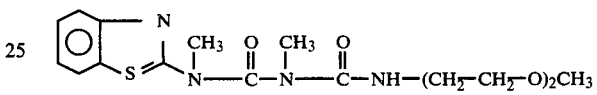

109 g (=60% of theory) of a solid of molecular mass 366 (M⊕ in the mass spectrum) are obtained from 110.5 g (0.5 mol) of 1-(benzo-1,3-thiazol-2-yl)-1,3-dimethylurea and 72.5 g (0.5 mol) of 3,6-dioxaheptyl isocyanate.

EXAMPLE 6

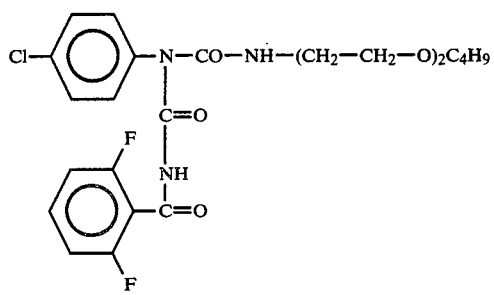

216 g (=87% of theory) of a solid are obtained from 155 g (0.5 mol) of N'-(4-chlorophenyl)-N-(2,6-difluorobenzoyl)-urea and 93.5 g (0.5 mol) of 3,6-dioxadecyl isocyanate; the $^1$H-NMR data of the solid shows that the acylurea adds the isocyanate onto the aryl-substituted NH and forms an N-acyl-biuret. The molecular mass is 497 (M⊕ in the mass spectrum).

EXAMPLE 7

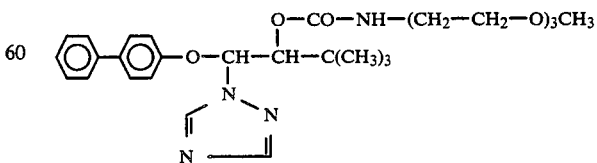

260 g (=99% of theory) of a solid of molecular mass 526 (the mass spectrum shows (M-isobutene)⊕ at 470) are obtained from 168.5 g (0.5 mol) of 3,3-dimethyl-2- hydroxyl-1-(4-phenyl-phenoxy)-1-(1,2,4-triazol-1-yl)-butane and 94.5 g (0.5 mol) of 3,6,9-trioxadecyl isocyanate.

EXAMPLE 8

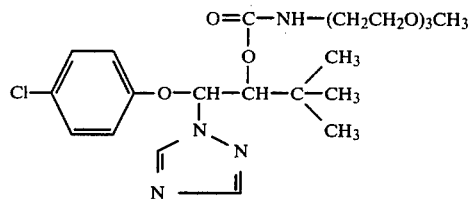

20.8 g (=87% of theory) of 1-(4-chlorophenoxy)-3,3-dimethyl-1-(1,2,4-triazol-1-yl)-2-(3,6,9-trioxadecylcarbamoyl)-butane, a viscous product of molecular mass 485 (M+ in the mass spectrum), are obtained from 14,8 g (0,05 mol) of 1-(4-chlorophenoxy)-3,3-dimethyl-1-(1,2,4-triazol-1-yl)-butane and 9.5 g (0.05 mol) of 3,6,9-trioxadecylisocyanate.

EXAMPLE 9

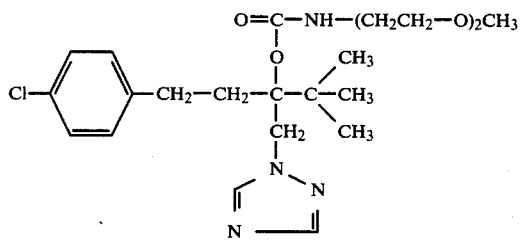

21.7 g (=96% of theory) of 1-(4-chlorophenyl)-4,4-dimethyl-3-(3,6-dioxaheptylcarbamoyl-3-(methylene-1,2,4-triazol-1-yl)-pentane, a viscous product of molecular mass 453 (M in the mass spectrum), are obtained from 15.4 g (0.05 mole) 1-(4-chlorophenyl)-4,4-dimethyl-3-(methylene-1,2,4-triazol-a-yl-pentane) and 7.25 g (0.05 mole) of 3,6-dioxaheptylisocyanate.

EXAMPLE 10

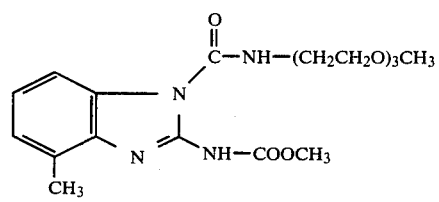

94.5 g (=96% of theory) of 4-methyl-1-(3,6,9-trioxadecylcarbamoyl)-2-benzimidazolylmethylcarbamate of molecular mass 394 (M+-32 in the mass spectrum), a solid having a melting point of 134° C., are obtained from 51.2 g (0.25 mole) of 4-methyl-2-benzimidazolylmethylcarbamate and 47.3 g (0.25 mole) of 3,6,9-trioxadecylisocyanate.

EXAMPLE 11

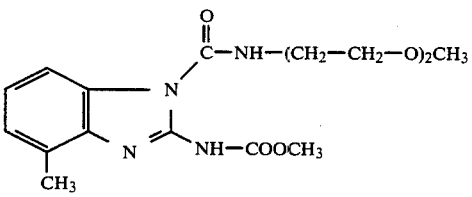

84.8 g (=97% of theory) of 1-(3,6-dioxaheptylcarbamoyl)-4-methyl-2-benzimidazolylmethylcarbamate of molecular mass 350 (M+ in the mass spectrum), a solid having a melting point of 187° C., are obtained from 51.2 g (0.25 mole) of 4-methyl-2-benzimidazolylmethylcarbamate and 36.3 g (0.25 mole) of 3,6-dioxaheptylisocyanate.

EXAMPLE A

Comparison of the Rate of Hydrolysis

The rate of degradation by hydrolysis was determined in i-propanol/water 1:1 at pH 7 and 40° C. The active compound concentration relates to the actual content of active compound (±2-3 ppm).

TABLE

| Compounds used | Example 1 (according to the invention) | ![structure] NHCOOCH3 | Example 4 (according to the invention) | ![structure] (known) |
|---|---|---|---|---|
| Initial concentration | 100 ppm | 100 ppm | 100 ppm | 100 ppm |
| After |  |  |  |  |
| 15 days | 80 ppm | 70 ppm | 85 ppm | 75 ppm |
| 30 days | 70 ppm | 60 ppm | 75 ppm | 60 ppm |
| 45 days | 60 ppm | 50 ppm | 70 ppm | 55 ppm |
| 60 days | 55 ppm | 40 ppm | 65 ppm | 50 ppm |
| 90 days | 45 ppm | 20 ppm | 50 ppm | 25 ppm |

It will be appreciated that the instant specification and examples are set forth by way of illustration and not limitation, and that various modifications and changes may be made without departing from the spirit and scope of the present invention.

What is claimed is:

1. A pest-combating agent of prolonged activity comprising the reaction product of a pest-combating agent having at least one hydrogen atom active in a Zerewitinoff reaction other than a hydrogen atom which is part of a carbamic acid ester group

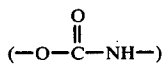

with a polyether isocyanate, the reaction with the polyether isocyanate taking place on said other hydrogen atom, the pest-combating agent being of the formula

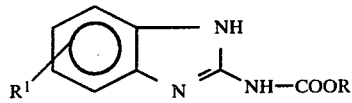

in which
R is $C_{1-4}$-alkyl, and
$R^1$ is $C_{1-6}$-alkyl or hydrogen.

2. A pest-combating agent of prolonged activity comprising the reaction product of a pest-combating agent having at least one hydrogen atom active in a Zerewitinoff reaction other than a hydrogen atom which is part of a carbamic acid ester group

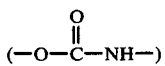

with a polyether isocyanate, the reaction with the polyether isocyanate taking place on said other hydrogen atom, said polyether isocyanate being of the formula

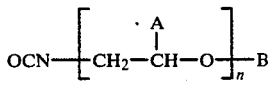

in which
A is hydrogen or methyl,
B is $C_{1-4}$alkyl or the radical $-C_{1-4}$-alkylene-NCO, and
n is an integer from 1 to 101.

3. A pest-combating agent of prolonged activity comprising the reaction product of a pest-combating agent having at least one hydrogen atom active in a Zerewitinoff reaction other than a hydrogen atom which is part of a carbamic acid ester group

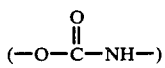

with a polyether isocyanate, the reaction with the polyether isocyanate taking place on said other hydrogen atom, said reaction product being 1-(3,6,9-trioxadecyl-carbamoyl)-2-benzimidazolylmethylcarbamate of the formula

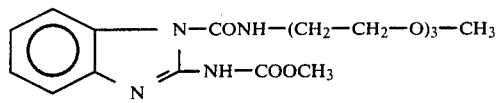

4. A process for the preparation of a pest-combating agent according to claim 1, comprising reacting a pest-combating agent having at least one hydrogen atom active in Zerewitinoff reactions other than a hydrogen atom is part of a carbamic acid ester group

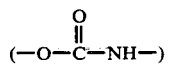

as defined in claim 1 with a polyether isocyanate.

5. A process for the preparation of a pest-combating agent according to claim 2, comprising reacting a pest-combating agent having at least one hydrogen atom active in Zerewitinoff reactions other than a hydrogen atom which is part of a carbamic acid ester group

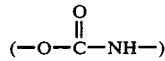

with a polyether isocyanate as defined in claim 2.

6. A process for the preparation of a pest-combating agent according to claim 3, comprising reacting a pest-combating agent having at least one hydrogen atom active in Zerewitinoff reactions other than a hydrogen atom which is part of a carbamic acid ester group

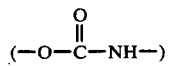

with a polyether isocyanate.

7. A pesticidal composition comprising a pesticidally effective amount of an agent according to claim 1, in admixture with a diluent.

8. A method of combating pests which comprises administering to such pests or to a pest habitat a pesticidally effective amount of an agent according to claim 1.

9. The method according to claim 8, wherein said agent is 1-(3,6,9-trioxadecyl-carbamoyl)-2-benzimidazolylmethylcarbamate.

10. A pesticidal composition comprising a pesticidally effective amount of an agent according to claim 2, in admixture with a diluent.

11. A method of combating pests which comprises administering to such pests or to a pest habitat a pesticidally effective amount of an agent according to claim 2.

12. The method according to claim 11, wherein said agent is 1-(3,6,9-trioxadecyl-carbamoyl)-2-benzimidazolylmethylcarbamate.

13. A pesticidal composition comprising a pesticidally effective amount of an agent according to claim 3, in admixture with a diluent.

14. A method of combating pests which comprises administering to such pests or to a pest habitat a pesticidally effective amount of an agent according to claim 3.

* * * * *